United States Patent [19]
Blanche et al.

[11] Patent Number: 6,153,597
[45] Date of Patent: Nov. 28, 2000

[54] PHARMACEUTICAL COMPOSITION USEFUL FOR NUCLEIC ACID TRANSFECTION, AND USE THEREOF

[75] Inventors: Francis Blanche; Béatrice Cameron, both of Paris; Joël Crouzet, Sceaux; Vincent Thuillier, Paris, all of France

[73] Assignee: Aventis Pharma S.A., Antony, France

[21] Appl. No.: 09/043,856

[22] PCT Filed: Sep. 27, 1996

[86] PCT No.: PCT/FR96/01516

§ 371 Date: Mar. 27, 1998

§ 102(e) Date: Mar. 27, 1998

[87] PCT Pub. No.: WO97/12051

PCT Pub. Date: Apr. 3, 1997

[30] Foreign Application Priority Data

Sep. 28, 1995 [FR] France ................................. 95 11411

[51] Int. Cl.[7] ................... A61K 31/711; A61K 31/7105
[52] U.S. Cl. ................ 514/44; 435/320.1; 435/455; 435/458; 435/325; 435/366; 530/350; 530/358; 530/387.1; 530/387.3; 536/23.1; 536/23.5; 536/24.5
[58] Field of Search ................... 435/320.1, 455, 435/458, 325, 366; 530/350, 358, 387.1, 387.3; 536/23.1, 23.5

[56] References Cited

U.S. PATENT DOCUMENTS 5,631,237  5/1997  Dzau et al. .......................... 514/44

FOREIGN PATENT DOCUMENTS

WO 94/25608  11/1994  WIPO.

OTHER PUBLICATIONS

Allen et al., FEB Letters, vol. 223, No. 1, pp. 42–46, Oct. 1987.
Dean et al., PNAS, vol. 91, pp. 11762–11766, Nov. 1994.
Farhood et al., Biochimica Et Brophysica Acta, vol. 1111, p. 239–246 (Abstract only), Nov. 1992.
Loeffler et al., Methods in Enzymology, vol. 217 pp. 599–618, 1993.
Boussif et al., PNAS, vol. 92, pp. 7297–7301, Aug. 1995.
Kaneda et al., J. Mol. Med., vol. 73, pp. 289–297, Jun. 1995.

*Primary Examiner*—David Guzo
*Attorney, Agent, or Firm*—Synnestvedt & Lechner LLP

[57] ABSTRACT

A pharmaceutical composition useful for nucleic acid transfection is disclosed. The composition contains, in addition to a nucleic acid and at least one transfection agent, at least one compound that combines DNA binding properties with a nuclear DNA vectorisation capability, and preferably belongs to the HMG ("High mobility group") protein family. The use of said composition for in vitro, ex vivo and/or in vivo nucleic acid transfer is also disclosed.

27 Claims, 2 Drawing Sheets

PHARMACEUTICAL COMPOSITION USEFUL FOR NUCLEIC ACID TRANSFECTION, AND USE THEREOF

The present invention concerns the field of gene therapy and relates more particularly to the in vitro, ex vivo and/or in vivo transfer of genetic material. The invention proposes, in particular, a novel pharmaceutical composition which is useful for transfecting cells efficiently. The invention also relates to the uses of this composition.

Chromosomal deficiencies and/or anomalies (mutation, aberrant expression, etc.) are the cause of many diseases of hereditary or non-hereditary nature. Conventional medicine has for a long time remained powerless in respect of them. Today, with the development of gene therapy, it is hoped henceforth to be able to correct or prevent this type of chromosomal aberration. This novel medication consists in introducing genetic information into the affected organ or cell, for the purpose of correcting this deficiency or anomaly or alternatively for the purpose of expressing a protein of therapeutic interest.

The main obstacle to the penetration of a nucleic acid into a target organ or cell lies in the size and the polyanionic nature of this nucleic acid, which oppose its passage across cell membranes.

Various techniques are nowadays proposed to remove this difficulty including, more particularly, the transfection of naked DNA across the plasma membrane in vivo (WO90/11092) and the transfection of DNA via a transfection vector.

As regards the transfection of naked DNA, its efficacy still remains very low. Naked nucleic acids have a short plasma half-life on account of their degradation by enzymes and their elimination via the urine.

As regards the second technique, two main strategies are proposed:
The first uses natural transfection vectors, namely viruses. It is thus proposed to use adenoviruses, herpesviruses, retroviruses and more recently adeno-associated viruses. These vectors prove to be of high transfecting performance but it is unfortunately not possible to exclude entirely, as far as they are concerned, certain risks of pathogenicity, replication and/or immunogenicity, which are inherent in their viral nature.
The second strategy consists advantageously in using non-viral agents capable of promoting the transfer and expression of DNA in eukaryotic cells.

The subject of the present invention lies more particularly in this second strategy.

Chemical or biochemical vectors represent an advantageous alternative to natural viruses, in particular on account of this absence of viral recombination and/or immunological response. They possess no pathogenic power, there is no risk of DNA multiplication within these vectors and there is no theoretical limit associated with them as regards the size of DNA to be transfected.

These synthetic vectors have two main functions, to condense the DNA to be transfected and to promote its cellular binding as well as its passage across the plasma membrane and, where appropriate, the two nuclear membranes.

On account of its polyanionic nature, DNA naturally has no affinity for the plasma membrane of cells, which is also polyanionic in nature. To overcome this drawback, non-viral vectors all generally possess polycationic charges.

Among the synthetic vectors developed, cationic polymers of polylysine and DEAE-dextran type, or alternatively cationic lipids or lipofectants, are the most advantageous. They possess the property of condensing DNA and of promoting its association with the cell membrane. More recently, the concept has been developed of targeted transfection, mediated by a receptor. This technique exploits the principle of condensing DNA, by virtue of the cationic polymer, while at the same time directing the binding of the complex to the membrane using chemical coupling between the cationic polymer and the ligand for a membrane receptor which is present at the surface of the cell type which it is desired to graft. Targeting of the transferrin or insulin receptor or of the hepatocyte asialoglycoprotein receptor have thus been described.

However, the synthetic vectors proposed nowadays are still far from performing as well as viral vectors. This may be the consequence in particular of insufficient condensation of the DNA to be transfected and/or difficulties encountered by the transfected DNA in leaving the endosome and penetrating into the cell nucleus. The reason for this is that the transport of DNA into the nucleus of a resting eukaryotic cell poses an obvious problem since the dimensions of the nuclear pores only allow the diffusion of proteins with a molecular weight below 60,000 Da (I. Davis et al., Ann. Rev. Biochem. 1995; 64; 865–896). A plasmid DNA having a molecular weight above $10^6$ therefore cannot naturally penetrate into the cell nucleus by simple diffusion.

The subject of the present invention is specifically to propose an advantageous solution to the abovementioned problem.

More precisely, the present invention proposes a pharmaceutical composition which is useful for the transfection of at least one nucleic acid, characterized in that it contains, besides the said nucleic acid and at least one transfecting agent, at least one compound which combines DNA-binding properties with a capacity for delivery of this DNA to the nucleus.

For the purposes of the invention, a compound which possesses DNA binding properties covers any compound capable of binding at least partially to the DNA to be delivered. As regards, more particularly, its ability to deliver this DNA, this is reflected for the purposes of the invention in an efficacy in directing this DNA efficiently across the various cell and/or nuclear membranes in order to convey it to the interior of the nucleus of the cell to be treated. The compound according to the invention may also appear, for example, in the form of a chimeric molecule which combines a DNA-binding domain with a domain which allows nuclear importation. In this particular case, a selection may be made, from among the DNA-fixing domains, of those derived from regulatory proteins capable of binding, for example, to specific sequences or, on the contrary, proteins known to possess a non-sequence-dependent affinity for DNA. As regards, more particularly, the domain involved in nuclear importation, this may be represented, for example, by a sequence referred to as nls (nuclear localization sequence). Such sequences may be similar to or derived from the deduced bipartite consensus sequence of nucleoplasmin or may be similar to or derived from the consensus sequence of the T antigen of SV40.

According to a particular embodiment, the invention relates to a pharmaceutical composition which is useful for the transfection of at least one nucleic acid, characterized in that it contains, besides the said nucleic acid and at least one transfecting agent, at least one compound belonging to the HMG family or one of its derivatives.

The proteins of HMG type, which stands for "high mobility group", are proteins rich in charged amino acids and possessing a molecular mass of less than 30,000 Da.

Being soluble in 2–5% perchloric acid, they are conventionally extracted from chromatin with 0.35 M NaCl.

3 families of HMG proteins are conventionally distinguished: proteins of type HMG1/2 with a molecular mass close to 25,000, HMG14/17 with a molecular mass close to 10–12,000, and HMGI/Y with a composition close to that of proteins of type HMG14/17, but whose tissue distribution during ontogeny is different. It is known that the primary sequence of the proteins is conserved during evolution within each of these three families.

As regards more particularly the proteins of the family HMG1/2, these are characterized by the presence of a predominantly basic sequence of 80 amino acids (net charge +20), referred to as the "HMG box", which constitutes a DNA-binding domain. In this family a distinction may be made between proteins capable of binding to specific sequences of double-stranded DNA and proteins whose binding specificity lies in a particular three-dimensional structure of DNA. In the first category are found the proteins UBF, SRY, TCF1 and ABF2, which stimulate the transcription of specific genes (Greiss E. A., et al. J. Mol. Evol. (1993) 37: 204–210). The sequence of each of these proteins contains one or more "HMG boxes". The second category is represented by the proteins HMG1 and HMG2. Their primary sequence is characterized by the presence of two "HMG boxes" and a C-terminal acidic sequence (Bustin M. B.B.A. (1990) 1049:231–243). These proteins bind specifically to palindromic DNA sequences extruded in cruciform structure (intrastrand pairing at the level of the palindrome) or to DNA sequences which have a high degree of curvature. These two types of structure have the common feature of widening the minor groove of DNA, which then becomes capable of accommodating the binding of proteins of type HMG1/2. The physiological role of the proteins HMG1 and HMG2 is to date poorly understood. It has, however, been shown that calf HMG1 protein is actively transported into the nucleus of mammalian cells (L. Kuehl et al.; J. Biol. Chem. 1985; 260, 10361–10368).

The Applicant demonstrated, unexpectedly, that it was possible to exploit these faculties of HMG proteins, namely their ability to bind DNA and to be actively transported into the nucleus, in order to promote effectively the transfection of heterologous nucleic acid sequences, which are associated with at least one transfecting agent, in the nucleus of cells to be treated.

For the purposes of the present invention, the term derivative denotes any peptide, pseudopeptide (protein incorporating non-biochemical components) or protein differing from the compound as defined above, obtained by one or more modifications of a genetic and/or chemical nature. Modification of a genetic and/or chemical nature may be understood to mean any mutation, substitution, deletion, addition and/or modification of one or more residues, for example, of the protein in question. More precisely, chemical modification is understood to mean any modification of the peptide or protein generated by chemical reaction or by chemical grafting of biological or non-biological molecule (s), onto any given number of residues in the protein. Genetic modification is understood to mean any peptide sequence whose DNA hybridizes with these sequences or fragments thereof and whose product possesses the activities indicated. Such derivatives may be generated for various purposes such as, in particular, that of increasing the affinity of the corresponding polypeptide for its DNA ligand, that of improving its levels of production, that of increasing its resistance to proteases, that of increasing and/or modifying one of its activities, or that of imparting novel pharmacokinetic and/or biological properties thereto. Among the derivatives resulting from an addition, mention may be made, for example, of chimeric peptide sequences containing an additional heterologous part attached to one end. The term derivative also comprises protein sequences homologous with the sequence in question, derived from other cell sources and in particular from cells of human origin, or from other organisms, and possessing an activity of the same type. Such homologous sequences may be obtained by hybridization experiments on the corresponding DNA. The hybridizations may be performed starting with nucleic acid libraries, using the native sequence or a fragment thereof as probe, under conventional conditions of stringency (Maniatis et al.), (cf. general techniques of molecular biology) or, preferably, under high stringency conditions.

In addition, within the context of the present invention, it may also be envisaged to exploit the strong affinity of some of the proteins of the HMG family, or of derivatives thereof, for secondary structures present on double-stranded DNA. These may in particular be four-stranded structures for which it has been shown in particular that rat HMG1 possesses a very strong affinity (Bianchi et al. Sciences, 1989, 243, 1056–1059). Such structures may also be obtained from natural sequences such as viral ITRs associated with adenoviruses, or alternatively they may be completely synthetic and obtained from artificial palindromes.

According to a preferred embodiment of the invention, the compound used is chosen from proteins of type HMG 1, 2, I, Y, 14 and 17 and derivatives thereof. It is more preferably represented by all or part of human HMG1 protein or one of its derivatives or homologues as defined above.

In a particularly advantageous embodiment, the compositions of the present invention also comprise a targeting element which allows the transfer of the nucleic acid to be guided. This targeting element may be an extracellular targeting element, allowing the transfer of nucleic acid to be guided towards certain desired tissues or cell types (tumour cells, liver cells, haematopoietic cells, etc.). It may also be an intracellular targeting element, allowing the transfer of nucleic acid to be guided towards certain preferred cell compartments (mitochondria, nucleus, etc.).

More preferably, the targeting element is bound, covalently or non-covalently, to the compound according to the invention. The targeting element may also be bound to the nucleic acid. According to a preferred mode of the invention, the said compound is associated, via an additional heterologous part bound at one of its ends, with a cell receptor ligand present at the surface of the cell type, such as, for example, a sugar, transferrin, insulin or the protein asialo-orosomucoid. It may also be a ligand of intracellular type such as a nuclear location signal sequence, nls, which promotes the accumulation of transfected DNA within the nucleus.

Among the targeting elements which can be used within the context of the invention, mention may be made of sugars, peptides, oligonucleotides or lipids. Such elements are preferably sugars and/or peptides such as antibodies or antibody fragments, cell receptor ligands or fragments thereof, receptors or receptor fragments, etc. In particular, they may be ligands for growth factor receptors, for cytokine receptors, for cell lectin receptors or for adhesion protein receptors. Mention may also be made of the receptor for transferrin, for HDLs and for LDLs. The targeting element may also be a sugar which makes it possible to target lectins such as the asialoglyco-protein receptors, or alternatively an antibody Fab fragment which makes it possible to target the receptor for the Fc fragment of immunoglobulins.

Advantageously the compound according to the invention may also be polyglycosylated, sulphonated and/or phosphorylated and/or grafted to complex sugars or to a lipophilic compound such as, for example, a polycarbon chain or a cholesterol derivative.

The composition according to the invention may, of course, comprise several compounds according to the invention, of different nature. Similarly, it may prove possible to combine the compound according to the invention with, besides the nuclear targeting compound described above, a second compound characterized by its capacity to compact DNA. Such compounds are described in particular in Application FR 95/01865.

The compound according to the invention is present in an amount which is sufficient to act with the nucleic acid according to the invention. Thus, the compound/nucleic acid ratio (expressed on a weight basis) may be between 0.01 and 5 and more preferably between 0.25 and 0.5.

As regards the transfecting agent present in the composition according to the invention, this is preferably chosen from cationic polymers and lipofectants.

According to the present invention, the cationic polymer is preferably a compound of general formula I

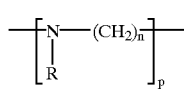 (I)

in which

R may be a hydrogen atom or a group of formula

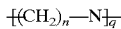

n is an integer between 2 and 10;

p and q are integers, it being understood that the sum p+q is such that the average molecular weight of the polymer is between 100 and $10^7$ Da.

It is understood that, in formula (I), the value of n may vary between the different units p. Thus, formula (I) embraces both homopolymers and heteropolymers.

More preferably, in formula (I), n is between 2 and 5. In particular, the polyethyleneimine (PEI) and polypropyleneimine (PPI) polymers have entirely advantageous properties. The preferred polymers for carrying out the present invention are those whose molecular weight is between $10^3$ and $5 \times 10^6$. By way of example, mention may be made of polyethyleneimine of average molecular weight 50,000 Da (PEI50K) or polyethyleneimine of average molecular weight 800,000 Da (PEI800K).

PEI50K and PEI800K are commercially available. As regards the other polymers represented by the general formula I, these may be prepared according to the process described in Patent Application FR 94/08735.

In order to obtain an optimum effect for the compositions of the invention, the respective proportions of the polymer and of the nucleic acid are preferably determined such that the molar ratio R=amines in the polymer/phosphates in the nucleic acid is between 0.5 and 50, more preferably between 5 and 30. Very particularly advantageous results are obtained using from 5 to 15 equivalents of polymer amines per nucleic acid charge.

As regards, more particularly, the lipofectants, these are amphiphilic molecules comprising at least one cationic hydrophilic region, for example polyamine, and one lipophilic region. The cationically charged, preferably polyamine, cationic region is capable of combining reversibly with the nucleic acid, which is negatively charged. This interaction compacts the nucleic acid greatly. The lipophilic region renders this ionic interaction inaccessible to the external aqueous medium, by coating the nucleolipid particle formed with a lipid film.

Advantageously, these lipofectants may also be chosen from lipopolyamines whose polyamine region corresponds to the general formula II

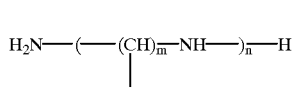 II in which m is an integer greater than or equal to 2 and n is an integer greater than or equal to 1, it being possible for m to vary between the different carbon groups lying between two amines. Preferably, m is between 2 and 6 inclusive and n is between 1 and 5 inclusive. Even more preferably, the polyamine region is represented by spermine, thermine or one of their analogues which has retained DNA-binding properties. As regards the lipophilic region, this is represented by at least one saturated or unsaturated hydrocarbon chain, cholesterol, a natural lipid or a synthetic lipid capable of forming lamellar or hexagonal phases, which is covalently bound to the hydrophilic region.

Patent Application EP 394,111 describes other lipopolyamines of general formula III which can be used within the context of the present invention

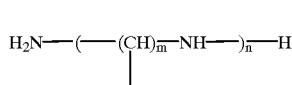 II in which R represents in particular a radical of general formula $(R_1R_2)N-CO-CH_2-NH-CO-$.

Representative examples of these lipopolyamines which may be mentioned more particularly are dioctadecylamidoglycylspermine (DOGS) and palmitoylphosphatidylethanolamine 5-carboxylspermylamide (DPPES).

The lipopolyamines described in Patent Application FR 94/14596 may also be used advantageously as transfecting agents according to the invention. They are represented by general formula III above in which R represents

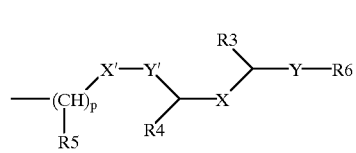 IV with

X and X' representing, independently of each other, an oxygen atom, a methylene group $-(CH_2)_q-$ with q equal to 0, 1, 2 or 3, or an amino group $-NH-$ or $-NR'-$ with R' representing a $C_1$ to $C_4$ alkyl group, Y and Y' representing, independently of each other, a methylene group, a carbonyl group or a C=S group, $R_3$, $R_4$ and $R_5$ representing, independently of each other, a hydrogen atom or a substituted or unsubstituted $C_1$ to $C_4$ alkyl radical, with p able to range between 0 and 5, $R_6$ representing a cholesterol derivative or an alkylamino group $-NR_1R_2$ with $R_1$ and $R_2$ representing, independently of each other, a saturated or unsaturated, linear or branched $C_{12}$ to $C_{22}$ aliphatic radical.

Representative examples of these lipopolyamines which may be mentioned most particularly are 2,5-bis(3-aminopropylamino)pentyl (dioctadecyl carbamoylmethoxy) acetate and 1,3-bis(3-aminopropylamino)-2-propyl (dioctadecylcarbamoylmethoxy)acetate.

Patent Applications EP 394,111 and FR 94 also describe a process which can be used for the preparation of the corresponding lipopolyamines.

In a particularly advantageous manner, dioctadecylamidoglycylspermine (DOGS), palmitoylphosphatidylethanolamine 5-carboxyspermylamide (DPPES), 2,5-bis(3-aminopropylamino)pentyl (dioctadecylcarbamoylmethoxy) acetate or 1,3-bis(3-aminopropylamino)-2-propyl (dioctadecylcarbamoylmethoxy)acetate may be used within the context of the invention.

In order to obtain an optimum effect of the compositions of the invention, the respective proportions of the polyamine and of the nucleic acid are preferably determined such that the ratio R of positive charges of the transfecting agent/negative charges of the nucleic acid is between 0.1 and 10 and more preferably between 0.5 and 2.

The presence of a compound according to the invention within a transfecting composition is advantageous in several respects. In particular, this results in markedly reduced toxicity, which subsequently makes possible, for example, the transfection of cells originally sensitive to the transfecting agent, such as, for example, haematopoietic cells with lipopolyamines.

In the compositions of the present invention, the nucleic acid may be either a deoxyribonucleic acid or a ribonucleic acid. Such nucleic acids are sequences of natural or artificial origin, and in particular genomic DNA, cDNA, mRNA, tRNA or rRNA, hybrid sequences or synthetic or semi-synthetic sequences. These nucleic acids may be of human, animal, plant, bacterial, viral, etc. origin. They may be obtained by any technique known to those skilled in the art, and in particular by screening libraries, by chemical synthesis or alternatively by mixed methods including the chemical or enzymatic modification of sequences obtained by screening libraries. They may moreover be incorporated into vectors, such as plasmid vectors.

As regards, more particularly, deoxyribonucleic acids, these may be single- or double-stranded. These deoxyribonucleic acids may code for therapeutic genes, sequences which regulate transcription or replication, antisense sequences, regions for binding to other cell components, etc.

For the purposes of the invention, the term therapeutic gene is understood to refer in particular to any gene coding for a protein product which has a therapeutic effect. The protein product thus encoded may be a protein, a peptide, etc. This protein product may be homologous with respect to the target cell (that is to say a product which is normally expressed in the target cell when the latter has no pathology). In this case, the expression of a protein makes it possible, for example, to overcome insufficient expression in the cell or the expression of a protein which is inactive or weakly active on account of a modification, or alternatively to overexpress the said protein. The therapeutic gene may also code for a mutant of a cell protein, which has increased stability, modified activity, etc. The protein product may also be heterologous with respect to the target cell. In this case, an expressed protein may, for example, supplement or provide an activity which is deficient within the cell, allowing the cell to combat a pathology or to stimulate an immune response.

Among the products which are therapeutic for the purposes of the present invention, mention may be made more particularly of enzymes, blood derivatives, hormones, lymphokines: interleukins, interferons, TNF, etc. (FR 92/03120), growth factors, neurotransmitters or precursors thereof or synthetic enzymes, trophic factors: BDNF, CNTF, NGF, IGF, GMF, aFGF, bFGF, NT3, NT5, HARP/pleiotrophin, etc.; apolipoproteins: ApoAI, ApoAIV, ApoE, etc. (FR 93/05125), dystrophin or a minidystrophin (FR 91/11947), the CFTR protein associated with cystic fibrosis, tumour-suppressing genes: p53, Rb, Rap1A, DCC, k-rev, etc. (FR 93/04745), genes coding for factors involved in coagulation: factors VII, VIII, IX, genes involved in DNA repair, suicide genes (thymidine kinase, cytosine deaminase), etc.

The therapeutic gene may also be an antisense gene or sequence, whose expression in the target cell makes it possible to control the expression of genes or the transcription of cellular mRNA. Such sequences may, for example, be transcribed in the target cell into RNA complementary to cellular mRNA and thus block their translation into protein, according to the technique described in Patent EP 140,308. The antisense sequences also comprise sequences coding for ribozymes, which are capable of selectively destroying target RNAs (EP 321,201).

As indicated above, the nucleic acid may also contain one or more genes coding for an antigenic peptide capable of generating an immune response in man or animals. In this particular embodiment, the invention thus makes it possible to produce either vaccines or immunotherapies applied to man or animals, in particular against microorganisms, viruses or cancers. The peptides may in particular be antigenic peptides specific for Epstein-Barr virus, for HIV virus, for hepatitis B virus (EP 185,573) or for pseudorabies virus or alternatively tumour-specific antigenic peptides (EP 259, 212).

The nucleic acid preferably also comprises sequences which allow expression of the therapeutic gene and/or of the gene coding for the antigenic peptide within the desired cell or organ. These may be sequences which are naturally responsible for expression of the gene in question when these sequences are capable of functioning in the infected cell. They may also be sequences of different origin (responsible for the expression of other proteins) or even synthetic sequences. In particular, they may be promoter sequences for eukaryotic or viral genes. For example, they may be promoter sequences derived from the genome of the cell which it is desired to infect. Similarly, they may be promoter sequences derived from the genome of a virus. In this respect, mention may be made, for example, of the promoters of the E1A, MLP, CMV, RSV, etc genes. In addition, these expression sequences may be modified by addition of activating sequences, regulatory sequences, etc.

Moreover, the nucleic acid may also contain, in particular upstream of the therapeutic gene, a signal sequence which directs the therapeutic product synthesized into the secretory pathways of the target cell. This signal sequence may be the natural signal sequence of the therapeutic product, but it may also be any other functional signal sequence, or an artificial signal sequence.

More preferably, the compositions of the invention also comprise one or more neutral lipids. Such compositions are particularly advantageous, in particular when the ratio R is low. The Applicant has, effectively, shown that the addition of a neutral lipid makes it possible to improve the formation of nucleolipid particles and, surprisingly, to promote the penetration of the particle into the cell by destabilizing its membrane.

More preferably, the neutral lipids used within the context of the present invention are lipids containing 2 fatty chains.

In a particularly advantageous manner, natural or synthetic lipids are used, which may be zwitterionic or devoid of ionic charge under physiological conditions. They may be chosen more particularly from dioleoylphosphatidylethanolamine (DOPE), oleoylpalmitoylphosphatidylethanolamine (POPE), distearoyl, -palmitoyl and -myristoylphosphatidylethanolamine and derivatives thereof N-methylated 1 to 3 times; phosphatidylglycerols, diacylglycerols, glycosyldiacylglycerols, cerebrosides (in particular such as galactocerebrosides), sphingolipids (in particular such as sphingomyelins) or alternatively asialogangliosides (in particular such as asialoGM1 and GM2).

These various lipids may be obtained either by synthesis or by extraction from organs (for example: the brain) or from eggs, by standard techniques which are well known to those skilled in the art. In particular, the extraction of natural lipids may be carried out using organic solvents (see also Lehninger, Biochemistry).

Preferably, the compositions of the invention, using a lipofectant as transfecting agent, comprise from 0.1 to 20 equivalents of neutral lipid per equivalent of lipopolyamine, and more preferably from 1 to 5. In the case where the transfecting agent is a cationic polymer, the compositions of the invention comprise, in addition to the cationic polymer in the ratios mentioned above, from 0.1 to 20 molar equivalents of neutral lipid per molar equivalent of nucleic acid phosphate, and more preferably from 1 to 5.

The compositions according to the invention may be formulated for the purpose of topical, cutaneous, oral, rectal, vaginal, parenteral, intranasal, intravenous, intramuscular, subcutaneous, intraocular, transdermal, etc. administration. The pharmaceutical compositions of the invention preferably contain a vehicle which is pharmaceutically acceptable for an injectable formulation, in particular for a direct injection into the desired organ, or for a topical administration (to skin and/or mucous membranes). They may in particular be sterile, isotonic solutions or dry compositions, in particular freeze-dried compositions, which, on addition, according to the case, of sterilized water or of physiological saline, allow injectable solutions to be made up. The doses of nucleic acid used for the injection and the number of administrations may be adapted in accordance with various parameters, and in particular in accordance with the mode of administration used, the pathology concerned, the gene to be expressed or the desired duration of the treatment.

The compositions may advantageously be used to transfect a wide variety of cell types such as, for example, haematopoietic cells, lymphocytes, hepatocytes, endothelial cells, melanoma cells, carcinomas and sarcomas, smooth muscle cells, neurons and astrocytes.

The present invention thus provides a particularly advantageous method for the treatment of diseases using the in vitro, ex vivo or in vivo transfection of a nucleic acid which is capable of correcting the said disease by combining with a transfecting agent of lipofectant or cationic polymer type, and a compound as defined above. More particularly, this method is applicable to diseases resulting from a deficiency in a nucleic acid or protein product, and the nucleic acid administered codes for the said protein product or contains the sequence corresponding to the said nucleic acid product. The compositions according to the invention are particularly advantageous on account of their bioavailability and their level of transfection.

The present invention also relates to any use of a compound according to the invention coupled to a cell receptor ligand, an antibody or antibody derivative, [lacuna] targeting a nucleic acid towards cells which express the corresponding receptors or antigens. From this standpoint, a potential ligand, antibody or antibody derivative is coupled to the said compound and the transfecting power of this chimeric molecule is evaluated in comparison with that of the compound alone.

The present invention will be described more fully with the aid of the examples which follow, which should be considered to be illustrative and non-limiting.

MATERIALS AND METHODS

Figure 1:
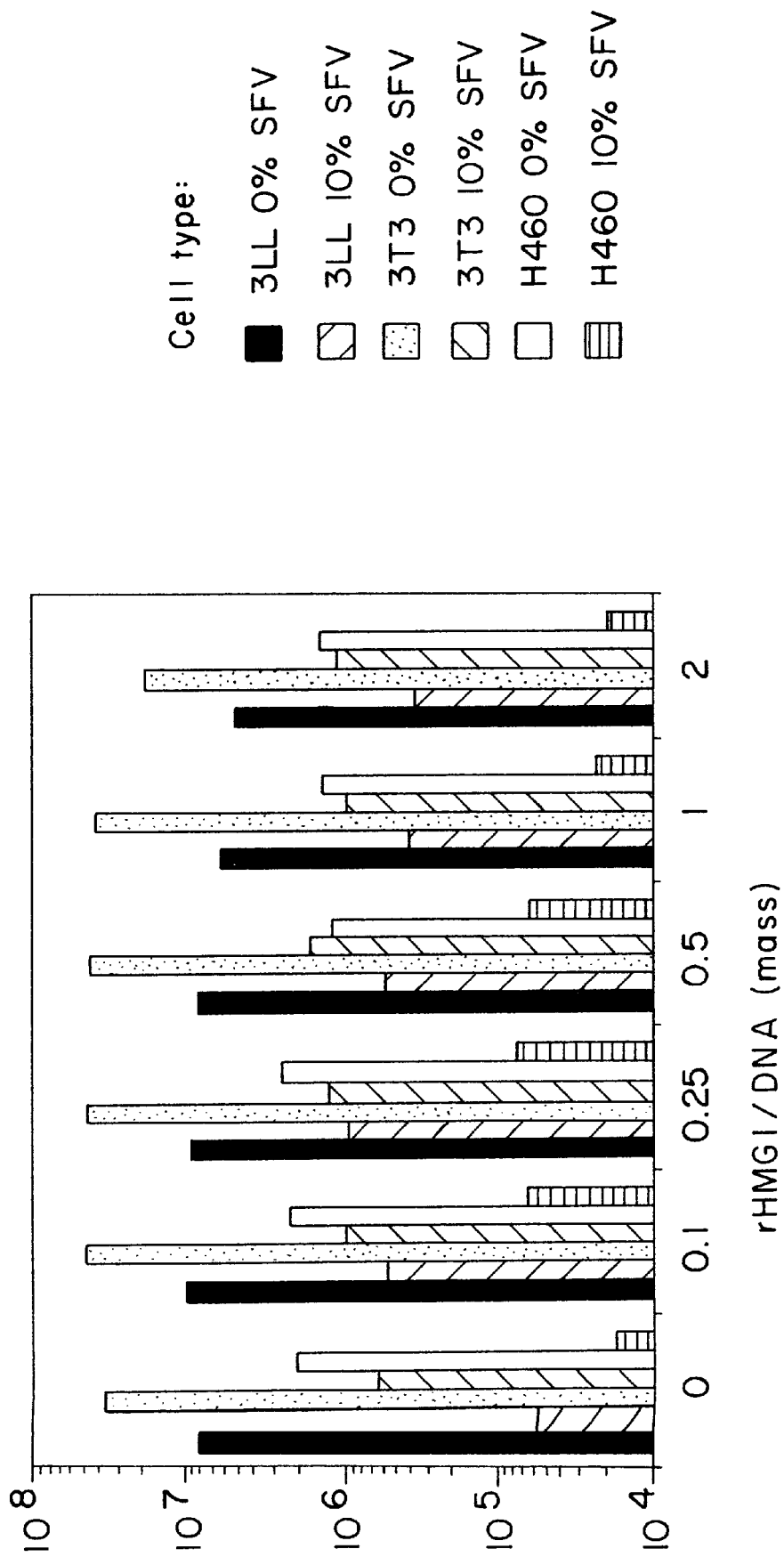
FIG. 1: Representation, in terms of light intensities, of the efficacy of transfections carried out according to the invention in various cell types.

The construction used to demonstrate the activity of the compositions of the invention is a plasmid containing the gene coding for luciferase (Luc), pCMV-Luc.

The plasmid pCMV-luc contains the cytomegalovirus (CMV) promoter, extracted from the vector plasmid pcDNA3 (Invitrogen) by cleavage with the restriction enzymes MluI and HindIII, located upstream of the gene coding for luciferase, inserted into the MluI and HindIII sites in the vector pGL basic Vector (Promega).

EXAMPLE 1

PREPARATION OF RAT HMG1 PROTEIN 1.1 Expression of HMG1 Protein in *E. coli*

This recombinant protein originating from a mammal was prepared by overexpression in *E. coli*.

The plasmid T7-RNHMG1 coding for rat HMG1 protein (M. E. Bianchi, *Gene*, 104 (1991) 271–275) is introduced into the *E. coli* strain BL21(DE3). The strain is subsequently cultured at 37° C. in LB medium+ampicillin (25 mg/L). A preculture is obtained from an isolated colony. This allows a 500 ml culture to be inoculated. When the absorbance of the culture at 600 nm reaches a value of 0.7, the synthesis of HMG1 is induced by addition of IPTG to a final concentration of 0.5 mM. The HMG1-producing strain is again cultured for 2 h 30 min in the presence of IPTG. The cells are then harvested by centrifugation (5000×g, 20 minutes), rinsed with 200 ml of distilled water and recentrifuged. The cell pellet is stored at −80° C. until purification.

1.2: Purification of the Recombinant HMG1 Protein

The HMG1 protein may be purified by chromatography from a culture of the *E. coli* strain described in Example 1.1, for example using the following procedure:

Except where otherwise indicated, the entire purification described below is carried out at 4° C. The cells obtained from 500 ml of culture are resuspended in 15 ml of 50 mM Tris/HCl buffer pH 7.7 containing 500 $\mu$M EDTA, 5 mM DTT, 200 $\mu$M Pefabloc SC [4-(2-aminoethyl) benzenesulphonyl fluoride hydrochloride] and 10% (weight/volume) glycerol. After breaking the cells by sonication for 15 min, the cell debris is separated by centrifugation (50,000×g; 1 h). The acellular extract is then chromatographed through a Sephadex G-25 column (Pharmacia) equilibrated and eluted with buffer A [20 mM Hepes pH 7.9 containing 400 mM sodium chloride, 200 mM EDTA, 1 mM DTT, 200 $\mu$M Pefabloc SC, 0.2% Nonidet P40 and 10% glycerol]. The fraction containing the proteins is collected and chromatographed through a column of DEAE-Sephadex A-25 gel (Pharmacia) equilibrated in buffer A. The protein fraction not retained on this column is progressively mixed with solid ammonium sulphate to a final concentration of 2.8 M. After 2 h, this suspension is centrifuged (30,000×g; 15 min). The supernatant is chromatographed at 20° C. through a Phenyl-Superose HR 5/5 column (Pharmacia) equilibrated in 20 mM Hepes buffer pH 7.9 containing 200 mM EDTA, 500 µM DTT and 2.8 M ammonium sulphate. The proteins are eluted from the column with a decreasing linear gradient of ammonium sulphate (2.8 M to 0 M) in the same buffer. The fractions containing the HMG1 protein are pooled and dialysed extensively against 50 mM Tris/HCl buffer pH 7.7 containing 1 mM EDTA and 500 µM DTT. This sample is then injected onto a MonoQ HR 5/5 column (Pharmacia) which is then eluted with a linear gradient of from 0 to 0.5 M sodium chloride in 50 mM Tris/HCl buffer pH 7.7–500 µM DTT. The protein HMG1, which forms a symmetrical absorbance peak at 280 nm, is collected in this buffer. The HMG1 protein is then taken up in 10 mM Mes buffer pH 6.2–140 mM NaCl-500 µM DTT after concentration by centrifugation in Centrikon 10. The HMG1 protein is stored at −80° C. until it is used. This preparation exhibits a single protein band migrating at an apparent molecular weight of 31,000 when it is analysed by electrophoresis under denaturing conditions (SDS) and visualization by Coomassie staining. The overall yield for the purification is 850 µg of pure HMG1 protein for 500 ml of starting culture.

EXAMPLE 2

IN VITRO TRANSFER OF NUCLEIC ACID INTO MAMMALIAN CELLS

This example shows how a protein, of type HMG1, binding to DNA and being actively imported into the nucleus, can be used to stimulate the transfection of plasmid DNA.

The construction used to demonstrate the activity of the compositions of the invention is the plasmid containing the gene coding for luciferase (Luc) described above.

The procedure is established for 24-well plates (ø 16 mm) to be harvested 2 days after transfection (confluent cells). All the parameters can be modified proportionally.

On day D, NIH 3T3 cells (ATCC: CRL1658), 3LL (Isakov N. et al., JNCI 71(1983) 139–145) H460 (Maxwell et al., Oncogene 8 (1993), 3421–3429) are inoculated at $10^5$ cells per well.

On day D+2 the cells are rinsed with PBS (to remove the traces of serum) and taken up in 250 ml of RPMI (3LL and H460) or DMEM (NIH 3T3), which may or may not be supplemented with 10% foetal calf serum (FCS).

Composition used for the transfection: the following are added into a tube, per well-equivalent:

$H_2O$ qs 20 ml

NaCl qs 140 mM final 0.5 mg plasmid DNA 125 ng HMG1 and the mixture is then vortexed moderately and incubated at room temperature for 15 minutes before adding 1.5 nmol of DOGS lipofectant. The mixture is again vortexed moderately and incubated at room temperature for 15 minutes.

The cells are transfected by addition of 20 ml of the DNA/HMG1/lipofectant mixture to the culture medium, and incubated for 2 to 4 hours at 37° C. This medium is then replaced by complete medium.

On day D+4, the cells are rinsed at room temperature with 250 ml of PBS and are lysed in 100 ml of ad hoc buffer (Reporter (Promega)+TCK and Aprotinin). 10 ml of lysate and 50 ml of substrate (Promega) are used to measure the activity of the luciferase synthesized.

Figure 2:
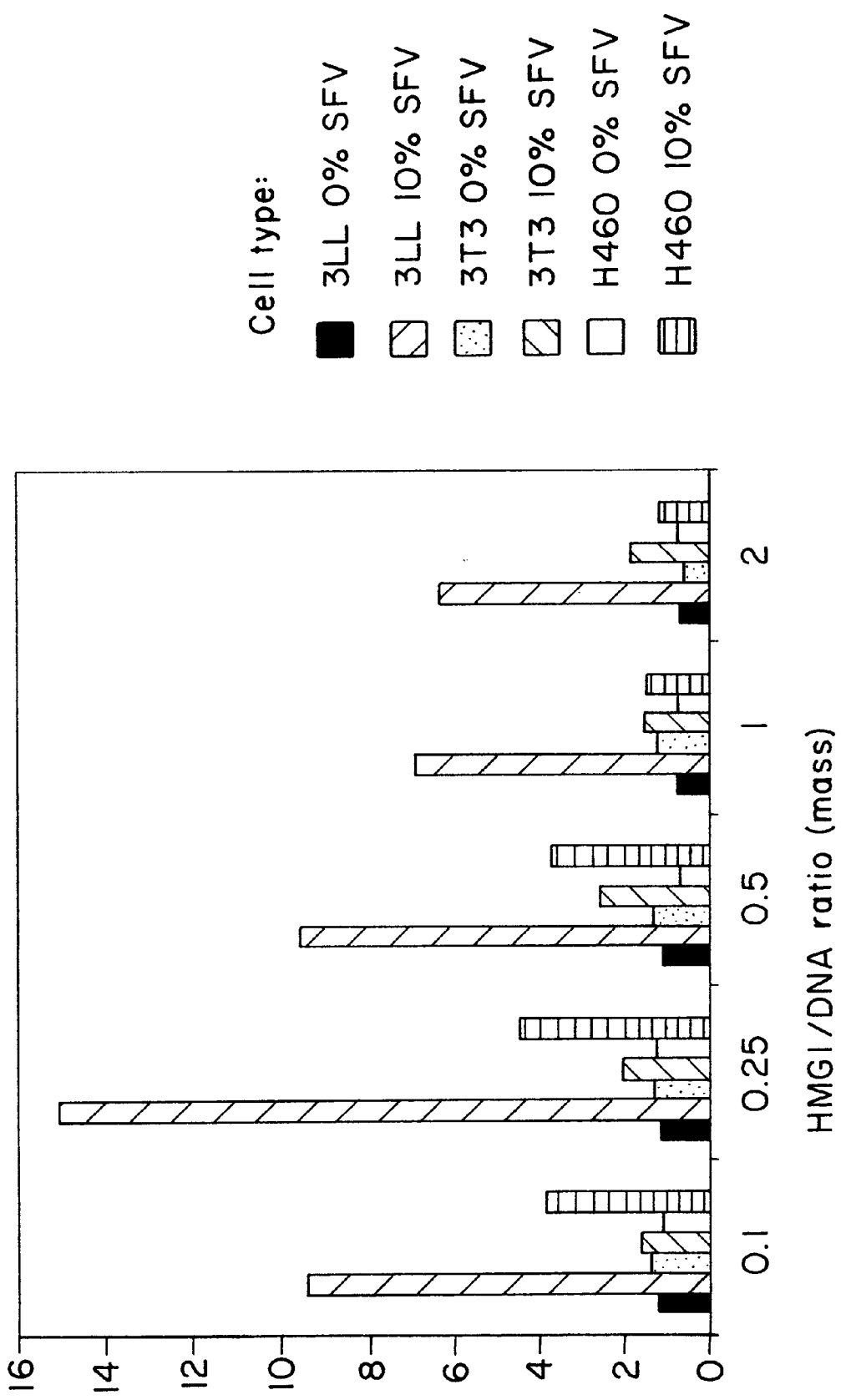
FIG. 2: Evaluation of the efficacy of transfections carried out in the presence and absence of HMG1.

The results presented in FIGS. 1 and 2 are the average of four experiments, repeated twice independently. To do this, the light units (LU) obtained by expression of the Luc gene in the transfected cells are evaluated.

FIG. 1 collates the values obtained for the three cell types mentioned above, in the presence of a variable amount of HMG1 protein.

FIG. 2 collates, in summary fashion, the factors for stimulation of transfection which are obtained by adding different amounts of HMG1 proteins. The increase in the efficacy of transfection by the HMG1 protein is variable depending on the cell type.

It is thus observed that the increase is at a maximum when the medium containing the composition necessary for the transfection is supplemented with 10% FCS. This is advantageous since the presence of FCS represents the conditions encountered in vivo. Moreover, it is significant that the presence of FCS decreases the efficacy of transfection, particularly in the absence of HMG1 protein. This suggests that the presence of FCS in the culture medium decreases the amount of DNA capable of being internalized by the cells. In this context, it may be inferred that HMG1 is particularly advantageous for transfection under conditions in which the amount of DNA is limiting.

The optimum HMG1/DNA ratio (by mass) for transfection is 0.25 to 0.5. Such conditions are not described as being capable of compacting DNA (Böttger M. et al., B.B.A. 950 (1988), 221–228); Stros M. et al., N.A.R. 22 (1994), 1044–1051). The reason for this is that the plasmid is not saturated with HMG1 (Kohlstaedt L. A. et al., Biochemistry 33 (1994), 12702–12707). The effect of the HMG1 protein is thus explained by its capacity to bind DNA and to be transported to the cell nucleus.

What is claimed is:

1. A composition for the transfection of nucleic acid into the nucleus of a cell, said composition comprising: the nucleic acid; a compound that binds at least partially to the nucleic acid and is capable of delivering nucleic acid to the nucleus; and a transfecting agent which is a cationic polymer or a lipopolyamine.

2. A composition according to claim 1, wherein the compound is polyglycosylated, sulphonated, phosphorylated and/or grafted to complex sugars or to a lipophilic agent.

3. A composition according to claim 1, wherein the compound is combined with a nuclear-receptor ligand or a cell-receptor ligand.

4. A composition according to claim 1, wherein the transfecting agent is a cationic polymer of general formula (I):

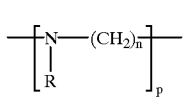

(I)

in which

R is a hydrogen atom or a group of formula

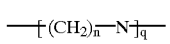

n is an integer between 2 and 10;

p and q are integers,
and the average molecular weight of the polymer is between 100 and $10^7$ Da.

5. A composition according to claim 1, wherein the transfecting agent is polyethyleneimine (PEI) or polypropyleneimine (PPI).

6. A composition according to claim 1, wherein the transfecting agent is a lipopolyamine comprising a hydrophilic polyamine region of general formula II:

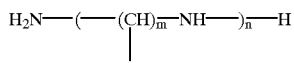

II in which m is an integer greater than or equal to 2, n is an integer greater than or equal to 1, and m is the same or different when n is greater than 1, wherein the hydrophilic polyamine region is covalently bound to a lipophilic region comprising a saturated or unsaturated hydrocarbon chain, cholesterol or a natural or synthetic lipid capable of forming lamellar or hexagonal phases.

7. A composition according to claim 1, wherein the transfecting agent is a lipopolyamine chosen from the group consisting of:

dioctadecylamidoglycylspermine (DOGS); palmitoylphosphatidylethanolamine 5-carboxyspermylamide (DPPES); 2,5-bis(3-aminopropylamino)pentyl (dioctadecylcarbamoylmethoxy)acetate; and 1,3-bis(3-aminopropylamino)-2-propyl (dioctadecylcarbamoylmethoxy)acetate.

8. A composition according to claim 1, wherein the nucleic acid is a deoxyribonucleic acid.

9. A composition according to claim 1, wherein the nucleic acid is a ribonucleic acid.

10. A composition according to claim 1, wherein the nucleic acid is chemically modified.

11. A composition according to claim 1, wherein the nucleic acid is an antisense sequence.

12. A composition according to claim 1, wherein the nucleic acid codes for a therapeutic protein.

13. A composition according to claim 1, which further comprises one or more neutral lipids.

14. A composition according to claim 1, wherein the compound is capable of directing the nucleic acid across a cell membrane or a nuclear membrane.

15. A process for the transfer of nucleic acid comprising the step of contacting a cell with a composition of claim 1.

16. A composition according to claim 5, wherein the cationic polymer is polyethyleneimine of average molecular weight 50,000 Da (PEI50K) or polyethyleneimine of average molecular weight 800,000 Da (PEI800K).

17. A composition according to claim 6, wherein the polyamine region is spermine, thermine or an analogue of spermine or thermine that has retained its nucleic acid-binding properties.

18. A composition according to claim 6, wherein the lipophilic region is represented by the general formula IV:

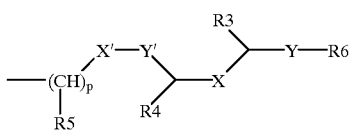

IV in which

X and X' represent, independently of each other, an oxygen atom, a methylene group —$(CH_2)_q$— with q equal to 0, 1, 2, or 3, or an amino group —NH— or —NR'— with R' representing a $C_1$ to $C_4$ alkyl group, Y and Y' represent, independently of each other, a methylene group, a carbonyl group or a C=S group, $R_3$, $R_4$ and $R_5$ represent, independently of each other, a hydrogen atom or a substituted or unsubstituted $C_1$ to $C_4$ alkyl radical, with p an integer from 0 to 5, and $R_6$ represents a cholesterol derivative or an alkylamino group —$NR_1R_2$ with $R_1$ and $R_2$ representing, independently of each other, a saturated or unsaturated, linear or branched $C_{12}$ to $C_{22}$ aliphatic radical.

19. A composition according to claim 7, wherein the transfecting agent is dioctadecylamidoglycylspermine (DOGS).

20. A composition according to claim 13, wherein the neutral lipid or lipids are synthetic or natural lipids that are zwitterionic or devoid of ionic charge under physiological conditions.

21. A composition according to claim 13, wherein the neutral lipid or lipids are chosen from the group consisting of:

dioleoylphosphatidylethanolamine (DOPE); oleoylpalmitoylphosphatidylethanolamine (POPE); distearoyl, -palmitoyl and -myristoyl-phosphatidylethanolamine and derivatives thereof N-methylated 1 to 3 times; phosphatidylglycerols; diacylglycerols; glycosyldiacylglycerols; cerebrosides; sphingolipids; and asialogangliosides.

22. A composition according to claim 21, wherein the neutral lipid or lipids are chosen from the group consisting of galactocerebrosides, sphingomyelins, asialoGM1 and asialoGM2.

23. A composition for the transfection of nucleic acid that comprises the nucleic acid, a compound belonging to the high mobility group ("HMG") family of proteins or a derivative thereof, and a transfecting agent chosen from the group consisting of cationic polymers and lipopolyamines.

24. A composition according to claim 23, wherein the compound is selected from the group consisting of proteins of type HMG1, 2, I, Y, 14 and 17 and derivatives thereof.

25. A composition according to claim 24, wherein the compound is represented by all or part of human HMG1 protein, its derivatives or homologues.

26. A composition according to claim 25, wherein the transfecting agent is dioctadecylamidoglycylspermine (DOGS).

27. A process according to claim 15, wherein the compound is coupled to a cell receptor ligand, an antibody or an antibody derivative.

* * * * *